(12) United States Patent
Kayser et al.

(10) Patent No.: US 11,596,301 B2
(45) Date of Patent: Mar. 7, 2023

(54) DEVICE FOR THE DETERMINATION AND ANALYSIS OF THE MOTOR SKILL AND THE OCULOMOTOR SKILL OF A PERSON

(71) Applicant: MOTOGNOSIS UG, Berlin (DE)

(72) Inventors: Bastian Kayser, Berlin (DE); Karen Otte, Berlin (DE); Sebastian Mansow-Model, Berlin (DE); Alexander Brandt, Berlin (DE)

(73) Assignee: MOTOGNOSIS UG, Berlin (DE)

( * ) Notice: Subject to any disclaimer, the term of this patent is extended or adjusted under 35 U.S.C. 154(b) by 199 days.

(21) Appl. No.: 16/652,048

(22) PCT Filed: Sep. 27, 2018

(86) PCT No.: PCT/EP2018/076294
§ 371 (c)(1),
(2) Date: Mar. 29, 2020

(87) PCT Pub. No.: WO2019/063706
PCT Pub. Date: Apr. 4, 2019

(65) Prior Publication Data
US 2020/0315449 A1 Oct. 8, 2020

(30) Foreign Application Priority Data
Sep. 29, 2017 (EP) ..................................... 17194130

(51) Int. Cl.
*A61B 3/113* (2006.01)
*H04N 13/204* (2018.01)
(Continued)

(52) U.S. Cl.
CPC ................ *A61B 3/113* (2013.01); *A61B 3/14* (2013.01); *A61B 5/1079* (2013.01); *A61B 5/112* (2013.01);
(Continued)

(58) Field of Classification Search
CPC ......... A61B 5/1124; A61B 3/113; A61B 3/14; A61B 5/1126; A61B 5/742;
(Continued)

(56) References Cited

U.S. PATENT DOCUMENTS 9,366,862 B2 * 6/2016 Haddick ................. G06F 3/011
2013/0095924 A1 4/2013 Geisner et al.
(Continued)

FOREIGN PATENT DOCUMENTS

CN 105026983 B * 7/2017 ............. G06V 40/20
KR 20150141461 A * 12/2015 ........... G06F 3/0304

*Primary Examiner* — Ryan R Yang
(74) *Attorney, Agent, or Firm* — JMB Davis Ben-David

(57) ABSTRACT

The invention relates to a device for the determination and analysis of the motor skill and the oculomotor skill of a person (100), with a headset comprising at least the following components: a display unit (9) for displaying an image to the eyes of a person (100), when the headset is mounted on the head of the person (100); an optical sensor system (3, 4, 6) for estimating the position and shape of an object in three-dimensional space and for estimating the position of the head set in three dimensional space, wherein the optical sensor system (3, 4, 6) is arranged and designed for the detection and registration of the hands and fingers of the person (100); an eye-tracking module (8) that is configured to determine a point of gaze of the person (100) wearing the device. The invention furthermore relates to various methods for using the device.

6 Claims, 3 Drawing Sheets

Figure 1:
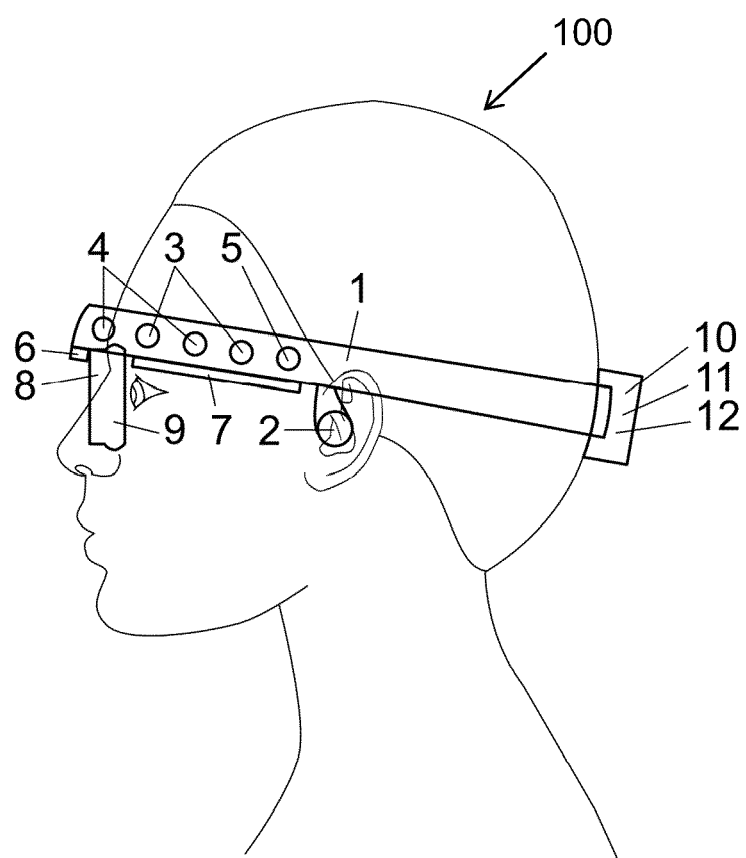

(51) Int. Cl.
  *H04N 13/344*  (2018.01)
  *A61B 3/14*  (2006.01)
  *A61B 5/107*  (2006.01)
  *A61B 5/11*  (2006.01)
  *A61B 5/00*  (2006.01)
  *G02B 27/01*  (2006.01)
  *G06F 3/01*  (2006.01)
  *G06T 19/00*  (2011.01)
  *G06F 3/00*  (2006.01)
  *G06V 40/20*  (2022.01)

(52) U.S. Cl.
  CPC ........... *A61B 5/1114* (2013.01); *A61B 5/1124* (2013.01); *A61B 5/1126* (2013.01); *A61B 5/742* (2013.01); *A61B 5/7405* (2013.01); *G02B 27/0172* (2013.01); *G06F 3/005* (2013.01); *G06F 3/011* (2013.01); *G06F 3/012* (2013.01); *G06F 3/013* (2013.01); *G06F 3/016* (2013.01); *G06T 19/006* (2013.01); *G06V 40/28* (2022.01); *H04N 13/204* (2018.05); *H04N 13/344* (2018.05); *A61B 2562/0219* (2013.01); *G02B 2027/0138* (2013.01); *G02B 2027/0141* (2013.01)

(58) Field of Classification Search
  CPC ........ A61B 2562/0219; G02B 27/0172; G02B 2027/0138; G02B 2027/0141; G06F 3/011; G06F 3/012; G06F 3/013; G06T 19/006; H04N 13/204; H04N 13/344
  See application file for complete search history.

(56) References Cited

U.S. PATENT DOCUMENTS

| | | |
|---|---|---|
| 2014/0372957 A1 | 12/2014 | Keane et al. |
| 2016/0169703 A1* | 6/2016 | Omr ..................... G01C 22/006 702/160 |
| 2017/0357332 A1* | 12/2017 | Balan ...................... G06F 3/017 |
| 2018/0008141 A1* | 1/2018 | Krueger .................. A61B 3/14 |
| 2018/0150147 A1* | 5/2018 | Fujimaki ................ G06F 3/038 |
| 2018/0246563 A1* | 8/2018 | Kunitomo ........... G02B 27/017 |
| 2020/0214559 A1* | 7/2020 | Krueger ................. A61B 3/113 |

* cited by examiner

DEVICE FOR THE DETERMINATION AND ANALYSIS OF THE MOTOR SKILL AND THE OCULOMOTOR SKILL OF A PERSON

CROSS-REFERENCE TO RELATED APPLICATIONS

This is the U.S. National Stage of International Patent Application No. PCT/EP2018/076294 filed on Sep. 27, 2018, which claims priority to European Patent Application No. 17194130.5 filed on Sep. 29, 2017.

The invention relates to a device for the determination and analysis of the motor skill and the oculomotor skill of a person. Furthermore, the invention relates to methods for the simultaneous and real-time determination of motor skills and oculomotor skills.

The determination of the motor skill of a person is of great importance in many applications such as for example in estimating the motor skill impairment after brain injury or an illness-related degradation of the motor skill.

In order to control his own body movements, a person needs to gain an accurate representation of his spatial surrounding. As spatial perception and interaction with objects in the surrounding of a person are predominantly controlled by the sense of sight, humans have evolved elaborate motor skills such as an eye-hand coordination (e.g. for grabbing objects), eye-head coordination, (for stabilizing the point of gaze) and also eye-body coordination (e.g. for obstacle avoidance).

It is known that impairment of the sense of sight such as for example missing gaze stabilization, impaired gaze movement, or focussing issues can have an impact on the coordinative skills of a person. Thus, there is a need for a combined assessment of the motor skill and the oculomotor skill of a person, wherein the oculomotor skill particularly refers to the control of gaze or gaze motion.

The oculomotor skill can be evaluated using commercially available devices, such as eye-tracking modules. The determination of the oculomotor skill is termed oculography.

In order to evaluate the oculomotor skill of a person, it is particularly important to determine the ability of the person to control the gaze in a defined manner. There are several test methods that are designed for assessing the oculomotor skill.

For the assessment of both, the motor skill or the oculomotor skill, it is required that the measurements are performed in a comparable way, repeatedly and independently of the surrounding. Therefore, the surrounding and the motor tasks have to be standardized.

In order to grant standardized measurement surroundings and motor tasks, so-called virtual-, augmented and/or mixed reality devices have been identified to serve this purpose. In the following augmented reality and mixed reality is referred to as augmented reality only.

Augmented or virtual reality devices are particularly suitable for generating standardized measurement conditions, as virtual surroundings can be either overlaid to the real surrounding (augmented reality) or completely replace the real surrounding (virtual reality).

These devices usually comprise some kind of wearable goggle device that is suited and arranged for displaying objects to the glasses or displays of the goggles.

For this reason, all these particularly augmented reality devices comprise at least one camera that records the surrounding and allows for a correct spatial representation of these displayed or overlaid objects in space. Furthermore, in some devices the position or movement of the body or the hands is simultaneously determined. Often, this is facilitated by an external device that records the person wearing the googles.

However, no such augmented reality device is configured to simultaneously determine the position of the eyes of the person wearing the device in real time.

Devices for tracking the eye, i.e. tracking the pupil of the eye, are for example disclosed in WO 2014209821 A1. Said application discloses an eye-tracking system with a head-mounted display, wherein in U.S. Pat. No. 8,998,414 B2 an integrated eye-tracking and display system is disclosed.

However, both of the above mentioned disclosures lack the ability of determining and evaluating hand postures. Hand postures would need to be evaluated with a separate device in order to measure motor skills such as the eye-hand coordination.

Furthermore, in order to measure the motor skill and the oculomotor skill of a person simultaneously, it is mandatory that for example the hand tracking can be performed with a high level of detail, i.e. it is not sufficient to solely determine a position of the hand, but it is equally important to determine the position of the fingers, and particularly their pointing direction, as the cooperation of motor skill and oculomotor skill is particularly important in tasks such as grabbing an object or pointing towards an object.

During evaluation it is also advantageous, if the measured data are accessible in real-time to a supervisor or the person performing the motor/oculomotor tasks for example to adapt the next tasks, or to assess the degree of impairment of the motor and/or oculomotor skill.

Therefore, solely the combination of existing devices is not solving the problem of providing a device for the simultaneous evaluation of the motor skill and oculomotor skill of a person, as it particularly proves problematic to synchronize data acquired from different, particularly non-connected devices, when recording motor skill and oculomotor skills. However synchronization of the data is of the essence, when the motor skill and the oculomotor skills are to be evaluated simultaneously.

Furthermore, the precise estimation and determination of interactions of a person with his surrounding is not possible with the devices known in the state of the art.

In this context, it is the objective of the present invention to overcome the problems of the state of the art.

Therefore, solely the combination of existing devices is not solving the problem of providing a device for the simultaneous evaluation of the motor skill and oculomotor skill of a person, as it particularly proves problematic to synchronize data acquired from different, particularly non-connected devices, when recording motor skill and oculomotor skills. However, synchronization of the data is of the essence, when the motor skill and the oculomotor skills are to be evaluated simultaneously.

According to the invention, the wearable and particularly portable device for the particularly simultaneous determination and analysis of the motor skill and the oculomotor skill of a person in real time comprises a headset, wherein the headset comprises at least the following components:
  a display unit for displaying an image particularly to each eye of the person, when the headset is mounted on the head of the person, wherein the image is configured such and displayed such to the eyes of the person, that a three-dimensional visual impression of the image is evoked,
  an optical sensor system for estimating the position and shape of an object in three-dimensional space and for the estimation of the headset's position in three dimensional space, wherein the optical sensor system is arranged and designed for the particularly marker-free detection and registration of the hands and fingers of the person particularly in the persons field of view, an eye-tracking module that is configured to determine a point of gaze, a stability of gaze and/or a motion of an eye relative to the head of the person wearing the device, and particularly an inertial measurement unit (IMU).

The device solves the problem according to the invention, as it combines a display unit, an optical sensor system as well as an eye-tracking module particularly mounted and interconnected on a headset, wherein the components are interconnected such, that it becomes possible to estimate the motor skill and the oculomotor skill of the person simultaneously, and repeatedly in a defined surrounding, wherein the defined surrounding can be particularly generated by the display unit.

An image in the context of the specification is particularly a stereo-image (also referred to as stereoscopic image in the following), that is an image that is composed of two different views of the same scene, wherein the different views are particularly shifted views of the scene, such that when displayed to the eyes of a person, said shifted views evoke a three-dimensional impression to the person.

An image can comprise a graphical representation of a virtual surrounding, i.e. it might be the complete surrounding of the person, as in virtual reality applications, or it might comprise only single graphical elements that are virtually arranged in the real surrounding of the person (augmented reality).

A display unit comprises for example an optical lens system with a projector, or a prism-based light guide system, that is configured for reproducing an image at an interface of the prism or to project it to a suitable screen.

Alternatively, a display unit can comprise a monitor, such as an LCD, an OLED-screen or another pixel-based screen.

Also, an optical waveguide-based display unit is conceivable as a suitable display unit for the device according to the invention.

Essentially any device or system that is suited to display an image to the eyes of a person and that is suitable to be mounted or comprised by a headset, i.e. being portable and wearable, is particularly comprised by the term "display unit" in the sense of the specification.

Displaying an image to the person refers to the overlaying or to the screening of an image to the person's eyes. This can be achieved on transparent (augmented reality), semi-transparent or non-transparent (virtual reality) material.

An optical sensor system comprises or is particularly a so-called time-of-flight (TOF) sensor that is configured to estimate a three-dimensional space information of the surrounding of the sensor. The information of the optical sensor system can be used to display an object with the display unit, i.e. an image comprising an object, wherein the object is arranged seamlessly in the surrounding. The term "seamlessly" refers to the fact that particularly size and perspective of the virtual object fit to the three-dimensional position it is arranged at in the (real) surrounding.

Alternatively, also a LIDAR or LADAR-system (the term "LIDAR" stands "Light Detection And Ranging, wherein the term "LADAR" stands for LAser Detection And Ranging) can be used in order to estimate a three-dimensional space information of the surrounding of the device/the person wearing the device.

Thus, the optical sensor system is particularly designed for the estimation of the three-dimensional space information of the surrounding of the device, wherein the three-dimensional space information is to be estimated particularly in the field-of-view of the person wearing the device.

Furthermore, the optical sensor system is particularly designed for the estimation of its relative position in three-dimensional space.

It is possible that the optical sensor system comprises two optical devices, wherein one device is configured and used for optical estimation of the surrounding and the second unit is configured and used for the registration of the hands and fingers.

As the optical sensor system is designed for particularly two purposes, the surrounding estimation and the position of itself. Both units are particularly 3D-cameras.

However, it is also conceivable that the optical sensor system is configured to estimate the three-dimensional space information of the surrounding based on a two-dimensional recording, i.e. a two-dimensional image, by analysis of the perspective of the image and other available information about the surrounding.

It is important that the optical sensor system is arranged and configured for the acquisition of data that allow a segmentation of body parts, such as a hand, a foot and fingers, to great detail, as otherwise it is not possible to determine accurate pointing directions or gestures (such as for example grabbing motions of the hand) that are important for evaluating the motor skills in combination with the data for the eye-tracking acquired from the eye-tracking module.

For this reason the optical sensor system particularly has a sampling rate of at least 30 Hz and provides image data with a spatial accuracy better than 1 cm.

The headset is configured to be carried on the head of a person, wherein the headset comprises means for stably mounting the headset on the head of a person.

The integration of all necessary sensor systems and components for the simultaneous estimation of motor skills and oculomotor skills in a single device, allows for the time-synchronized determination of said data without said data for example being ported or migrated between different devices. All data can be handled and bundled in a single data stream and evaluated and analysed in real time.

The device according to the invention allows for the synchronous and simultaneous estimation and determination of for example eye-hand coordination, eye-head coordination, and also eye-body coordination.

The eye-tracking module is particularly designed for the determination of the pupils relative to the face or the head, such that a point of gaze can be determined, particularly for each eye.

The eye-tracking system should exhibit a sampling rate of at least 120 Hz and provide eye orientations with an accuracy of better than 1°.

According to another embodiment of the invention, the device is wireless and thus can be carried around without physical constraints.

The device is particularly portable, i.e. the device weights particularly less than 1 kg.

This embodiment increases the flexibility of use of the device, particularly as all necessary components for the estimation of the motor skill and the oculomotor skill are arranged on the headset or on the device.

In order to maintain autonomous and portable operation of the device, the device particularly comprises a battery pack, wherein the battery pack has means arranged at the battery pack that allow the battery pack to be carried around with the person, such as for example a back-pack that allows arranging the battery pack on the back of the person. The battery pack can also be integrated to the device itself.

According to another embodiment of the invention, the device comprises a computer, wherein the computer is configured to process the recorded data from the components and to control and execute a computer software program that is particularly configured for the estimation of motor skills and oculomotor skills.

The computer can be arranged such that it can be carried on the back of the person, or it can be integrated in the headset. Particularly as the computational complexity increases, when segmenting hand and fingers recorded by the optical sensor system, it might become necessary to arrange the computer, particularly equipped with batteries for autonomous operation, in a back-pack that can be carried on the back of the person wearing the headset.

The computer is connected to the components on the headset for example by wire.

As the increased processing power is particularly required by the detailed segmentation of the hand for identification of the fingers or the pointing direction, the computer can for example be a laptop computer that is suitable for being transported in a back-pack.

The term "computer" in this specification refers to an electronic device that particularly comprises a CPU, and/or a microprocessor unit as well as an electronic memory storage. A computer is configured to be programmed, reprogrammed and to be able to execute computer program code that is loaded or streamed on the computer. Furthermore, a computer in the sense of the current specification is configured to process the data from the components of the device, particularly in real time.

A computer can comprise batteries.

According to another embodiment of the invention, the display unit comprises a transparent or semi-transparent screen, wherein the image is displayable or projectable, for example by a prism, a waveguide or other means, on the transparent or semi-transparent screen or to the eyes, wherein the display unit is particularly comprised in an augmented reality module.

This augmented reality embodiment is particularly useful, as the device can be built significantly lighter, as no (e.g. pixel-based) video screens for displaying are needed. Also, the energy consumption of such a device is lower as compared to virtual reality devices.

Also, a potentially alienating effect of a virtual reality device can be avoided, as the person is still capable of seeing his real surrounding through the transparent or semi-transparent screen. In virtual reality devices the real surrounding can only be recorded and displayed on the (non-transparent) screens, which might nonetheless lead to a feeling of isolation with the person wearing the device.

As augmented reality modules are commercially available, it is particularly advantageous to provide the device according to the invention with such an augmented reality module.

The augmented reality module can also comprise the optical sensor system in order to record and evaluate the surrounding of the person wearing the device.

The augmented reality module particularly is an augmented reality device that is configured for displaying augmented reality objects on the screen.

The screen can be transparent, which means that it is optically transparent particularly in the visible region of the electro-magnetic spectrum (e.g. 400 nm-680 nm).

The images can be displayed on such a transparent screen for example by the surface reflectivity or other physical parameters that allow a display of images on a transparent material. Also, it is possible to project the image directly to the eyes of the person, so that no specific property of the screen material is required.

The term "semi-transparent" refers to the property of the screen of being transparent only in a region of the visible spectrum, e.g. 400 nm to 580 nm, such that the image can be displayed on the screen with wavelength lying outside said region. This will enhance the contrast of the displayed image.

Furthermore, the term "semi-transparent" can also refer to the fact that the transparency of the screen is less than 90%, particularly less than 50%, more particularly less than 10%, particularly over the whole range of the visible spectrum.

According to an alternative embodiment of the invention, the display unit comprises a particularly pixel-based screen that is arranged in front of the eyes of the person, when the person is wearing the device, and wherein an image is displayable on the screen.

This virtual reality embodiment allows for a better control over the surrounding displayed to the person, i.e. the whole evaluation and determination of the motor skills and oculomotor skills can be performed in a very repeatable manner, particularly independent of the real surrounding of the person, as the images displayed to the person comprise the complete visually perceivable surrounding of the person. Visual interference with the real surrounding is avoided.

This embodiment allows for a greater flexibility in test conditions. It can for example be visually simulated, i.e. displayed to the person that the person is moving in a certain direction while this is not true in reality.

Such test conditions are only achievable by the virtual reality embodiment.

According to another embodiment of the invention, the headset comprises a stereo-camera system for recording the surrounding of the person, particularly the field of view of the person, and wherein device according to the invention is configured such that the recording of the stereo-camera system is displayable on the screen of the display unit, particularly such that a three-dimensional impression of the surrounding is evoked at the person wearing the device The optical sensor system is or comprises particularly said stereo-camera system.

The recording of the stereo-camera system might be processed such that for example additional graphical objects are displayed to the eyes of the person.

According to another embodiment of the invention, the headset comprises a camera for recording the surrounding of the person, particularly the field of view of the person, wherein the device according to the invention is particularly configured such that the recording of the camera is displayable on the screen of display unit.

This embodiment can be used alternatively to the stereo-camera system or additionally to the stereo-camera system.

Also here it is possible to process the recordings of the camera for example to add some additional graphical objects to be displayed to the person.

According to another embodiment of the invention, the headset comprises an inertial measurement unit (IMU), wherein the inertial measurement unit is arranged such that it is sensitive to a motion or to an inclination of the head of the person and wherein the inertial measurement unit is configured to determine the inclination and/or the motion of the head, when the person wears the device, wherein the inertial measurement unit particularly comprises a gyroscope and an accelerometer.

The advantage of a device comprising such an inertial measurement unit is that the combination of the recorded field-of view of the optical sensor system with the data acquired by the inertial measurement unit, the position and orientation of the head and the point of gaze can be determined with higher accuracy as compared to an optical sensor system or inclination sensor alone.

The inertial measurement unit can be configured to also record data of the body movements, i.e. the inertial measurement unit particularly comprises a body motion sensor system, as disclosed in the following embodiment.

According to another embodiment of the invention the device comprises a body motion sensor system configured for measuring and determining movements of the body of the person, wherein the movements are particularly translational, swaying and/or rotational movements of the body.

The combination of the device according to the invention with a body motion sensor system is particularly advantageous, as for the determination of the motor skills of a person particularly for the determination of the eye-body coordination (together with the eye-tracking module), it is important to determine the body movements.

Said body motion sensor system can be an IMU. As IMUs can be integrated in a chip, this embodiment is particularly robust and can be incorporated in the device according to the invention particularly cost-efficient.

The body motion sensor system is particularly arranged at the torso of the person, in order to be able for example to separate the motion of the head from the motion of the body. For this reason the body motion sensor system is particularly not comprised in the headset of the device.

However it is also possible to estimate a body/torso motion with the inertial measurement unit of the headset. The accuracy however is increased when a dedicated (body-) body motion sensor system is comprised by the device.

The body motion sensor system can also be a 3D-sensor, such as a time-of-flight camera, or a stereo-camera that is arranged such at the device, particularly at the headset, that the 3D-sensor points downwards and is configured to record the surrounding, particularly the floor. Motions of the body can then be derived from these recordings.

Similarly, the body motion sensor system comprises an image- or a depth-sensor, wherein the image- or depth-sensor is oriented and arranged such on the headset that at least a part of a foot of the person is encompassed by a recordable field of view of the image- or depth-sensor, when the headset is mounted on the head, particularly wherein the part of the foot can be at least temporarily captured, when the headset is mounted on the head and the person wearing the device is walking.

The 3D-sensor can be arranged in the same way as the image- or depth-sensor.

When the body motion sensor system comprises an optical device, such as for example an image- or depth-sensor or a 3D-sensor, the sensor can be arranged at the headset, particularly at a visor of the device. For example, it is possible to arrange one camera at the left side of the visor and a second camera at the right side of the visor such that stereoscopic images can be acquired and evaluated.

Furthermore, with an optical device as a body motion sensor system arranged for recording at least a part of the foot of the person, it is possible to track one foot or both feet, which enables the metric analysis of the gait of the person. This feature goes beyond the possibilities of a body motion sensor system based on an accelerometric device, such as an accelerometer, or an IMU.

According to another embodiment of the invention, the headset comprises a microphone and/or a loudspeaker, such as an earphone, or headphones.

This embodiment allows the communication of the person wearing the device with a particularly remotely located operator of the device.

Furthermore, it is possible to play sounds particularly for indicating the achievement of a task or to estimate the hearing abilities of the person in correlation for example with the position of gaze.

According to another embodiment of the invention, the headset comprises a processor, wherein the processor is designed for the real-time or close to real time signal processing, of signals from the components.

Said processor can be comprised in a computer or be a separate processor. The latter provides the advantage that the weight of the headset is minimized with respect to a computer.

According to another embodiment of the invention, the device comprises a radio frequency transmitter for transmitting radio signals to an external device, wherein the signals comprise information on the recorded and estimated data from the device. Furthermore, the transmitted data can also comprise the communication between a remotely located operator and the person wearing the device.

According to another aspect of the invention, the device comprises batteries, wherein the batteries are arranged in a bag, a belt, a back-pack or a hip-pack.

The problem according to the invention is furthermore solved by a method for analysing particularly simultaneously the motor skill and the oculomotor skill of a person in real-time particularly with a device according to the invention. The method comprising the steps of:
- Estimating a three-dimensional surrounding of the person, particularly with the optical sensor system of the device, comprising for example a camera, a time-of-flight sensor or another sensor that is disclosed in the context of the optical sensor system;
- Displaying an object arranged in the three-dimensional space surrounding the person, particularly with the display unit of the device according to the invention,
- Determining the position and shape of the hand and the fingers of the person pointing towards the displayed object particularly with the optical sensor system,
- Determining a pointing direction or a virtual point of contact of the object and a finger of the person from the position and shape of the hand and the fingers,
- Determining a deviation of the pointing direction and the position of the displayed object.

The three-dimensional estimation of the surrounding of the person can be facilitated for example with a so-called SLAM-algorithm (SLAM stands for "Simultaneous Localization And Mapping"). Having a three-dimensional representation of the surrounding, a particularly three-dimensional image is displayed to the user, wherein the image comprises or is said object. The object is virtually arranged in the three-dimensional surrounding, particularly while the objects proportions and particularly the objects lighting correspond to the appearance of a real object at the position. The object is thus virtually arranged in three dimensions and can be a three- or two-dimensional object itself.

Therefore, the person wearing the device is seeing the surrounding and the displayed object. The surrounding can be a completely virtual surrounding (an image representing the surrounding).

With the optical sensor system and/or other optical systems the hand and the fingers of the person are captured. The captured image(s) are processed by a segmentation algorithm, such as for example taught in "*Accurate, Robust, and Flexible Realtime Hand Tracking*", Sharp et al, 2015". Downstream of the segmentation, the position (relative to the surrounding and/or the object) and the shape of the hand, and at least the position, shape and/or pointing direction of one finger, particularly of more fingers of the hand, are estimated.

Devices that are configured to estimate a hand position are often times not configured for the detailed estimation of the finger positions, shape and/or pointing direction. This estimation requires more computational power than most augmented reality devices or virtual reality devices offer.

Thus, besides the ability to record the surrounding and segment the hand and fingers, the device according to the invention provides sufficient processing power in order to estimate the pointing direction of the fingers in real-time or close to real-time.

As the position, shape and pointing direction is estimated, it is particularly estimated, whether the person is trying to grab or point towards the displayed object.

From the position of the object, the position, and pointing direction of the hand and fingers, it is possible to determine a deviation from the pointing direction from the actual object position.

This deviation can be for example a distance, particularly an Euclidean distance.

When the displayed object is moving, the deviation can also be lag time between the pointing of the fingers and the objects position.

Furthermore, it is possible to determine the deviation between the pointing direction of the hand and/or fingers and object position, particularly continuously, intermittently or repeatedly. By such kind of analysis, it is possible to particularly identify a tremor.

According to another embodiment of the invention, the method further comprises the steps of:

Determining a point of gaze particularly with the eye-tracking module of the device according to the invention, Determining, whether the person looks toward the displayed object.

This embodiment allows for the correlated estimation of a point of gaze in the above outlined test scenarios. Also here it is possible to determine a deviation of the point or direction of gaze and the objects position.

This deviation can also be measured in terms of a Euclidean distance or in an angular deviation. Furthermore, similar to the estimation of the pointing direction of the hand, for example a tremor or a motoric lag time can be identified.

The results of both deviation estimations can be the base for further tests.

According to another embodiment of the invention, the displayed object is moving along a predefined trajectory and particularly the deviation of the pointing direction of the hand, fingers and/or the eyes and the position of the displayed object is determined continuously or in predefined time intervals.

The problem according to the invention is also solved by a method for estimating the step length, step frequency, symmetry of gait, and/or the cadence of a person with a device according to the invention, comprising the steps of:

Determining with at least one component of the device according to the invention, particularly the inertial measurement unit, the body motion sensor system, the camera and/or the stereo-camera system the motion of the head of a walking person wearing the device, Determining a walking speed of the person wearing the device with at least one component particularly with the body motion sensor system, the camera and/or the stereo-camera system, Determining from the determined walking speed and the motion of the head, a step length and a step frequency.

The method advantageously allows the determination of the step length and step frequency particularly with a single, portable device.

According to another embodiment of the invention, the method further comprises the step of:

Determining the position and shape of the feet of the person with the 3D-sensor of the body motions sensor system.

This embodiment allows the additional estimation of gait width and enhances reliability and accuracy of step length and step frequency, particularly when combined with data about the spatial position and orientation of the headset as provided by for example the IMU.

According to another embodiment of the invention, the gait width, the symmetry of gait and/or the cadence of the person walking is determined from the data acquired from the at least one component.

According to another embodiment of the invention, the method further comprises the steps of:

Providing a predefined minimum step length and a minimum step frequency,

Displaying a virtual object to the person with the display unit, when the determined step length and/or step frequency is lower than the predefined minimum step length and/or step frequency, wherein the object is particularly displayed at a location in the surrounding that lies in the way of walking of the person, and/or Providing an audio signal to the person, when the determined step length and/or step frequency is lower than the predefined minimum step length and/or step frequency, wherein said audio signal is particularly provided by means of a speaker comprised in the headset.

This embodiment allows indicating a person wearing the device that his step length or frequency is below a predefined minimum value.

Furthermore, this embodiment is particularly advantageous as the so-called "freeze of gait" in Parkinson disease can be overcome. It is known that a Parkinson-affected person, whose gait is starting to freeze or is frozen, can overcome this state by an obstacle put in the way of walking.

The method according to the invention solves this problem by displaying an object that can be placed at a position that would pose an obstacle to the person, if the person would walk further, wherein the object can be an obstacle that would require a step up or down in order to be overcome by the person. Alternatively or additionally a sound signal can be provided to the person.

According to another embodiment of the invention, the sound signal is repeated particularly with the frequency of gait that has been estimated prior the frequency dropped below the minimum frequency. This "stepping-metronome" can be especially effective.

The sound signal is particularly shorter than the period of the step frequency and can be a beep.

According to the invention, the whole process of recognizing a freeze of gait is automated, as well as the positioning of the object in the way of walking of the person.

The problem according to the invention is furthermore solved by a method for determining eye movements and hand tremor with a device according to the invention, comprising the steps of:

Determining the eye movements of the person wearing the device with the eye-tracking module, Determining the position and shape of the hands of the person wearing the device with the optical sensor system, Comparing the determined eye movement and the determined position and shape of the hands.

The problem is furthermore solved by a method for determining irregular eye movements and irregular hand movements with a device according to the invention, comprising the steps of:

Determining an eye movement of the person with the eye-tracking module,

Determining the position and shape of the hands of the person wearing the headset, Comparing the determined eye movement and the determined movement and/or shape of the hands against one or more predefined temporospatial parameters and/or patterns.

Irregular is in this context refers to a temporospatial deviation of eye movement and/or hand movement from predefined parameters and/or temporospatial patterns.

In the following the invention is illustrated by means of a detailed figure description and exemplary embodiment.

It is shown in

Figure 2:
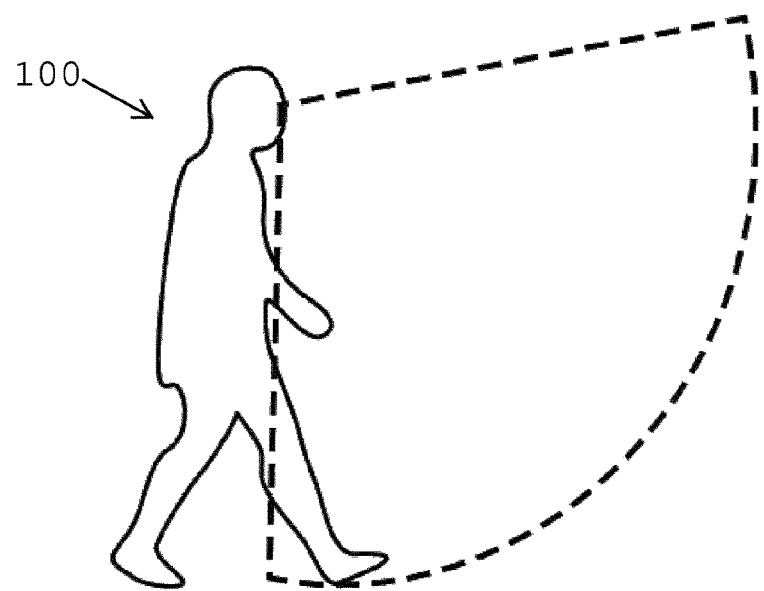
Figure 2:
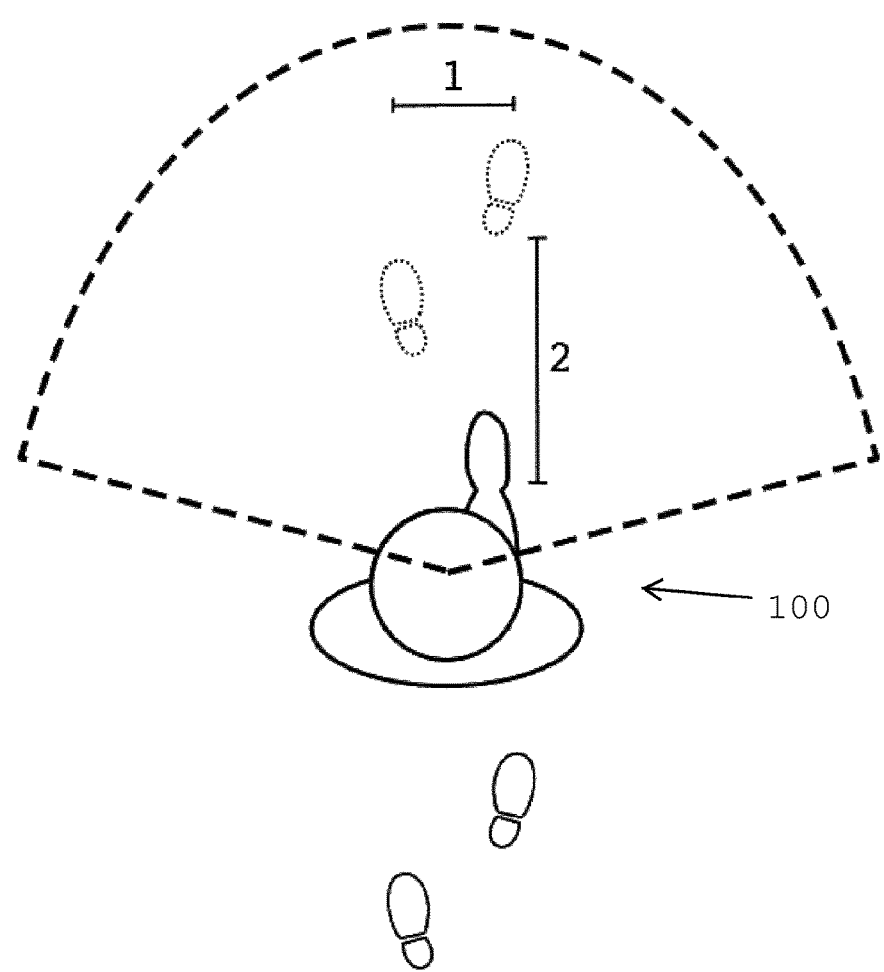
Figure 3:
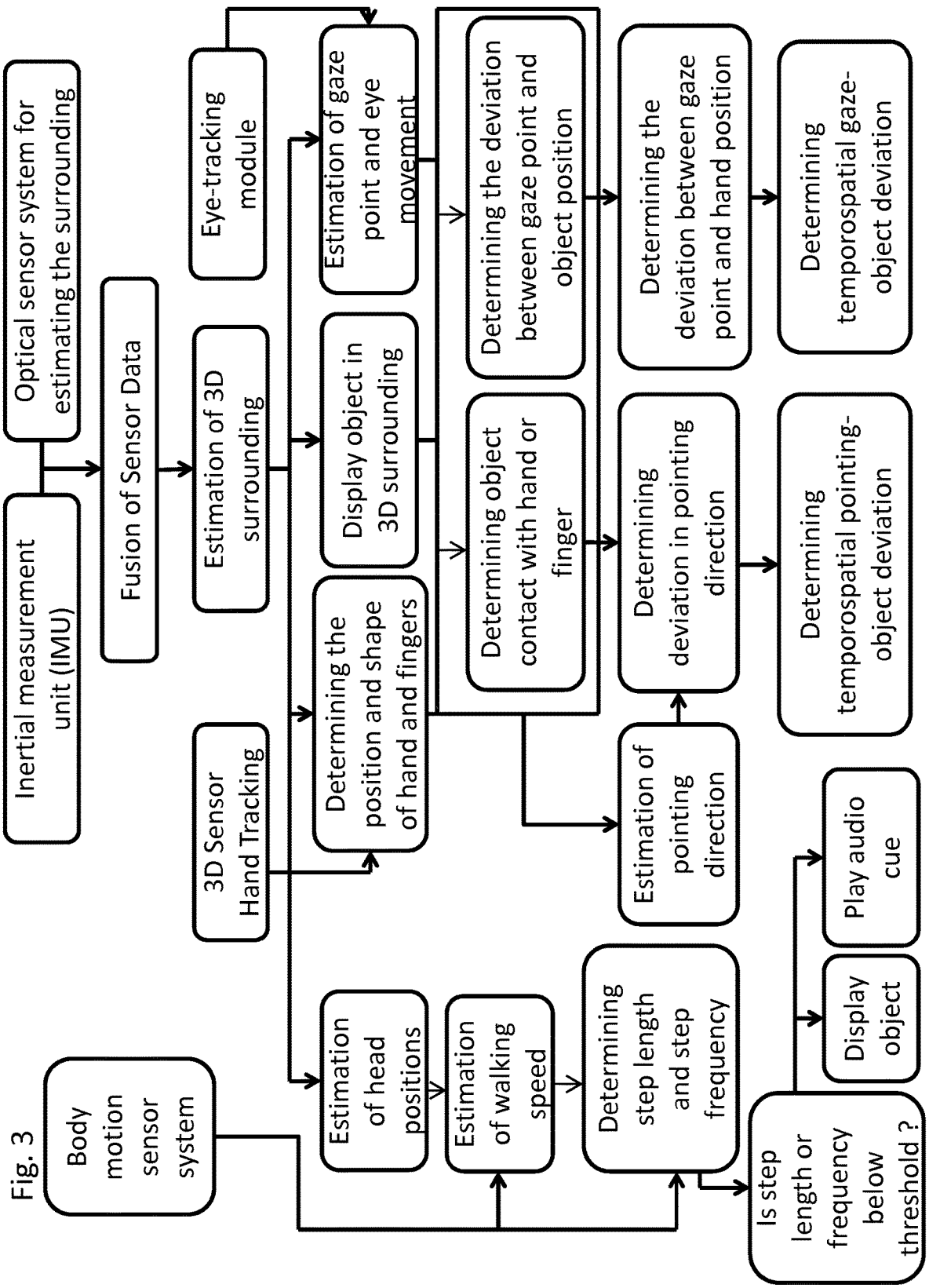

FIG. 1 a schematic drawing of the device according to the invention;

FIG. 2 Illustration of the downward pointing sensor field of view;

FIG. 3 flowchart depicting the parameters estimated by the various methods according to the invention, and how these parameters are determined form the measurement data acquired by the components of the device.

In FIG. 1 the device according to the invention is shown schematically. The device comprises a headset that is worn on the head of the person.

The headset comprises a headband 1 that is configured to stably arrange the headset above the eyes of the person. The headband 1 can be made of rubber or another elastic material. However, also other length-adjustable textile materials are suitable. The headband 1 might comprise a means for adjusting the length.

Speakers 2 are comprised by the headset, wherein the speakers 2 in this example are formed as headphones 2, which plug in the ear. With the headphones 2 audio signals, operator instructions or other sounds can be transmitted to the person.

Furthermore, the device comprises forward oriented optical sensors for estimating the position in three dimensional space; the sensors each can be an IMU.

Additionally the headset comprises forward oriented optical sensors 4 for hand and finger tracking.

Furthermore, an IMU 5 is arranged at the headband 1.

The headband comprises a downward oriented optical sensor 6, also referred to a body sensor, for estimating the position in three-dimensional space and for body, feet and hand tracking.

A microphone or a microphone array 7 for recording the voice of the person is arranged at the headband 1.

An eye tracking module 8 for determining the eyes position is integrated in the headset as well. Also, a display unit 9 is arranged in front of the eyes, so that images or instructions can be displayed to the person wearing the headset.

At the backside of the headset, a computing unit 10 is arranged, that also comprises an IMU 11 and a battery 12.

All electronic and electric components, such as the optical sensors 3, 5 and 6, the eye tracking module 8, the headphones 2 and the display unit 9 are connected to the computing unit 10 and can be controlled by the computing unit 10.

In FIG. 2 a visualization (a side view and a top view) of measurement area (schematically indicated by broken lines) of the 3D body sensor (see FIG. 1 ref. 6) is shown. The 3D body sensor points downwards and is configured to record the surroundings, particularly the floor, the body limbs feet and the hands, all of which are visible to the sensor during normal walk and the floor. Motion signals of the specific body parts can then be derived from these recordings. Hands and feet are visible to the sensor during normal walk. By usage of the surrounding information, speed and body movement data, the spatial foot positions are measured and computed over time. From these foot position signals, gait parameters like step and stride length, as well as the step width can be calculated. Further derived parameters include for example the cadence (steps per minute), the knee amplitude (mean amplitude of knee movements in anterio-posterior direction), the knee amplitude asymmetry (log of the ratio between the knee amplitudes from the smaller body side and the larger body side, see Nantel et al., Gait & Pos 34(2011) 329-333), the maximum stride time (maximum time needed to perform one stride as the mean of both body sides), the coefficient of variation of the stride time, the stride time asymmetry (log of the ratio between stride time from the faster body side and the slower body side, see Nantel et al., Gait & Pos 34(2011) 329-333), the hand amplitude (mean amplitude of hand excursions in anterio-posterior direction), the hand amplitude asymmetry (log of the ratio between the hand amplitudes from the smaller body side and the larger body side, see Nantel et al., Gait & Pos 34(2011) 329-333) and the coefficient of variation of the hand swing time.

Since the 3D body sensor directly provides spatial coordinates of specific body parts, corresponding specific amplitude parameters and relative distances between body parts like width can be computed, in contrast to the IMU accelerator based data, from which only time and frequency parameters can be generated.

FIG. 3 shows a flowchart for the methods according to the invention. The determined parameters and variables can be used in subsequent evaluation methods.

Boxes that exhibit a dotted background refer to components of the device according to the invention, wherein the arrows indicate the transfer and/or provision of measurement data acquired by the respective component.

Arrows between plain boxes (no dotted background) indicate method steps for determining the respective parameter listed in the box or to achieve the result listed in the box the arrow points to.

In case a decision has to be made the box is diamond shaped and lists the decision that has to be made. The various possible outcomes of the decision is indicated by arrows leading away from the diamond shaped box.

The invention claimed is:

1. Method for analyzing the motor skill and the oculomotor skill of a person (100) with a device, comprising the steps of:

Estimating a three dimensional surrounding of the person with the device,

Displaying an object arranged in the three-dimensional space surrounding the person with the display unit of the device, Determining the position and shape of the hand and the fingers of the person pointing towards the displayed object with the optical sensor system, Determining a pointing direction or a point of contact of the object and a finger of the person from the position and shape of the hand and the fingers, Determining a deviation of the position of the hand or the pointing direction of the fingers and the position of the displayed object, wherein the devise comprises:

a headset, a display unit (9) for displaying an image to the eyes of a person (100), when the headset is mounted on the head of the person (100), an optical sensor system (3, 4, 6) for estimating the position and shape of an object in three-dimensional space and for estimating the position of the head set in three dimensional space, wherein the optical sensor system (3, 4, 6) is arranged and designed for the detection and registration of the hands and fingers of the person (100), an eye-tracking module (8) that is configured to determine a point of gaze of the person (100) wearing the device.

2. Method according to claim 1, wherein the method further comprises the steps of:

Determining a point of gaze with the eye-tracking module,

Determining a deviation between the point of gaze and the objects position.

3. Method according to claim 1, wherein the displayed object is moving along a predefined trajectory, the method further comprises the steps of:

Determining a temporospatial deviation between the position of the hand or the pointing direction of the fingers and the displayed object trajectory, Determining a temporospatial deviation between the point of gaze and the displayed object trajectory.

4. Method according to claim 1, wherein the method further comprises the steps of:

Providing a predefined minimum step length and a minimum step frequency,

Displaying an object to the person with the display unit, when the determined step length and/or step frequency is lower than the predefined minimum step length and/or step frequency, and/or Issuing an audio signal particularly with an audio unit such as a speaker comprised by the headset, when the determined step length and/or step frequency is lower than the predefined minimum step length and/or step frequency.

5. Method for determining eye movements and hand tremor with a device comprising the steps of:

Determining the eye movements with the eye-tracking module,

Determining the position and shape of the hands of the person wearing the device with the optical sensor system, Comparing the determined eye movement and the determined position and shape of the hands, wherein the devise comprises:

a headset, a display unit (9) for displaying an image to the eyes of a person (100), when the headset is mounted on the head of the person (100), an optical sensor system (3, 4, 6) for estimating the position and shape of an object in three-dimensional space and for estimating the position of the head set in three dimensional space, wherein the optical sensor system (3, 4, 6) is arranged and designed for the detection and registration of the hands and fingers of the person (100), an eye-tracking module (8) that is configured to determine a point of gaze of the person (100) wearing the device.

6. Method for determining irregular eye movements and irregular hand movements with a device, comprising the steps of:

Determining an eye movement of the person with the eye-tracking module,

Determining the position and shape of the hands of the person wearing the headset, Comparing the determined eye movement and the determined movement and/or shape of the hands against one or more predefined temporospatial parameters and/or patterns, wherein the devise comprises:

a headset, a display unit (9) for displaying an image to the eyes of a person (100), when the headset is mounted on the head of the person (100), an optical sensor system (3, 4, 6) for estimating the position and shape of an object in three-dimensional space and for estimating the position of the head set in three dimensional space, wherein the optical sensor system (3, 4, 6) is arranged and designed for the detection and registration of the hands and fingers of the person (100), an eye-tracking module (8) that is configured to determine a point of gaze of the person (100) wearing the device.

* * * * *